US00PP37512P2

(12) United States Plant Patent
Biancheri

(10) Patent No.: US PP37,512 P2
(45) Date of Patent: Jul. 7, 2026

(54) ***RANUNCULUS* PLANT NAMED 'AB TEPEYO'**

(50) Latin Name: *Ranunculus asiaticus*
Varietal Denomination: AB TEPEYO

(71) Applicant: Biancheri Creazioni Societa' Semplice Agricola, Camporosso Mare (IT)

(72) Inventor: Alberto Biancheri, Camporosso Mare (IT)

(73) Assignee: Biancheri Creazioni Societa' Semplice Agricola (IT)

( * ) Notice: Subject to any disclaimer, the term of this patent is extended or adjusted under 35 U.S.C. 154(b) by 0 days.

(21) Appl. No.: 19/357,321

(22) Filed: Oct. 14, 2025

(51) Int. Cl.
*A01H 5/02* (2018.01)
*A01H 6/72* (2018.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP30,272 P3 * 3/2019 Biancheri ..... A01H 5/02
Plt./263.1

* cited by examiner

*Primary Examiner* — Karen M Redden

(57) ABSTRACT

A new and distinct cultivar of *Ranunculus* plant named 'AB TEPEYO' is disclosed. characterized by petal colored Light Yellowish Pink (RHS 37D) with a Deep Pink (RHS 48B, 48C to 48D) border and Light-Yellow Green (RHS 145D and 154D) near the base. Flower petals are durable. Flower stems are 30 to 35 cm long. The new variety is a *Ranunculus*. normally produced as a cut flower and potentially useful as an ornamental plant.

2 Drawing Sheets

Figure 1:
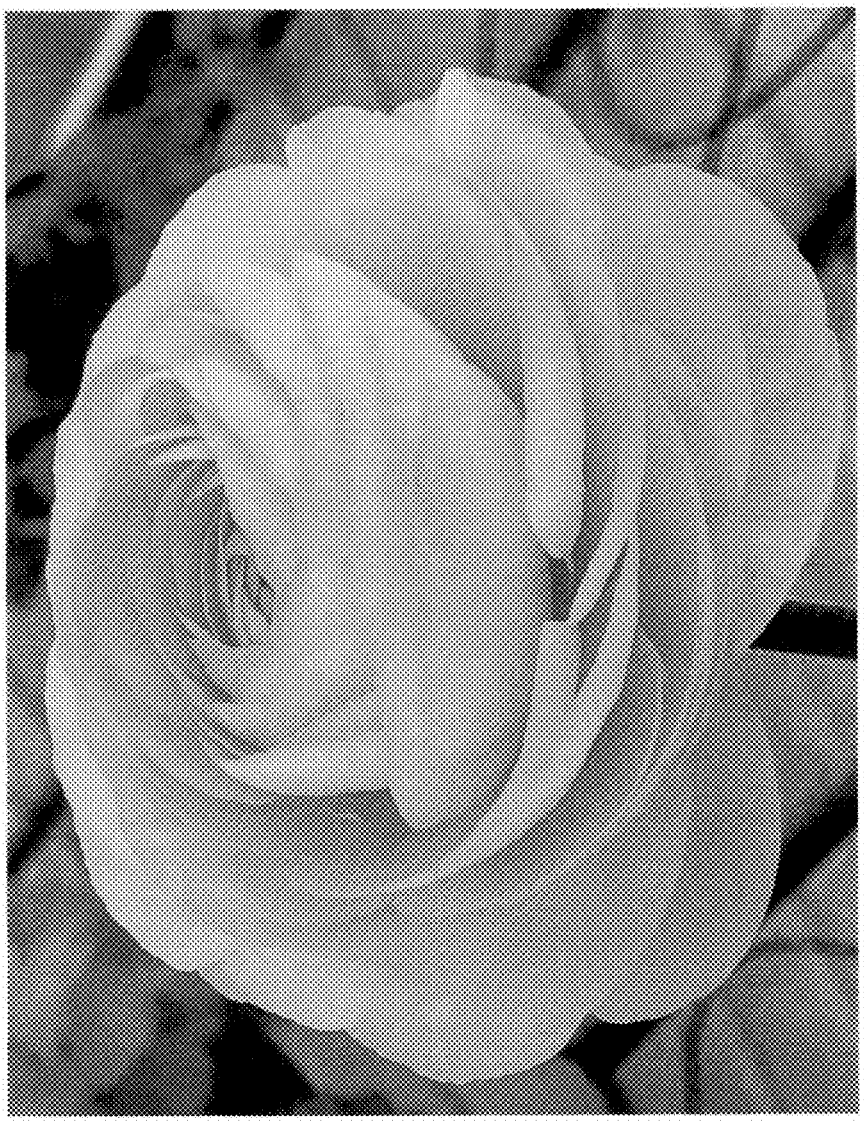

Latin name of the genus and species: *Ranunculus asiaticus*.

Variety denomination: 'AB TEPEYO'.

BACKGROUND OF THE INVENTION

The new *Ramunculus* cultivar is a product of a planned breeding program conducted by the inventor, Alberto Biancheri at a research nursery in Camporosso Mare, Italy. The cross resulting in this new variety was made during 2016.

The seed parent is an unnamed, unpatented, proprietary *Rammculus asiaticus*. The pollen parent is a different unnamed, unpatented, proprietary *Rammculus asiaticus*. The new variety was selected in 2019 by the inventor in a group of seedlings resulting from the 2016 crossing, in a research greenhouse in Camporosso Mare, Italy.

Asexual reproduction of the new cultivar was first performed by vegetative division of buds sprouting from the rhizome of the selected plant. Subsequent propagation has been performed by tissue culture. First propagation took place at a research greenhouse in Camporosso Mare, Italy in 2019 and has shown that the unique features of this cultivar are stable and reproduced true to type in multiple successive generations.

SUMMARY OF THE INVENTION

The cultivar 'AB TEPEYO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'AB TEPEYO' These characteristics in combination distinguish 'AB TEPEYO' as a new and distinct *Rammculus* cultivar:

1. Petal color is Light Yellowish Pink (RHS 37D) with a Deep Pink (RHS 48B, 48C to 48D) border and Light-Yellow Green (RHS 145D and 154D) near the base.
2. Vegetative, herbaceous plant habit.
3. 30 to 35 cm long flower stems.
4. Durable flower petals.

PARENT COMPARISON

Plants of the new cultivar 'AB TEPEYO' are similar to plants of the seed parent, in most horticultural characteristics, however, plants of the new cultivar 'AB TEPEYO' differ in the following;

1. Flower petals of the new cultivar are a light yellowish pink with a darker pink border; flower petals of the seed parent are a darker pink without marginal coloration.

Plants of the new cultivar 'AB TEPEYO' are similar to plants of the pollen parent, in most horticultural characteristics, however, plants of the new cultivar 'AB TEPEYO' differ in the following;

1. Flower petals of the new cultivar are a light yellowish pink with a darker pink border; flower petals of the pollen parent are a darker pink without marginal coloration.

COMMERCIAL COMPARISON

Plants of the new cultivar 'AB TEPEYO' are comparable to the unpatented commercial variety *Ranunculus*

'ABPERKONS'U.S. Plant Pat. No. 30,272. The two *Ranunculus* varieties are similar in most horticultural characteristics; however, the new variety 'AB TEPEYO' differs in the following:

1. Petal color of the new cultivar is light Yellowish Pink (RHS 37D) with a Deep Pink (RHS 48B, 48C to 48D) border and Light-Yellow Green (RHS 145D/154D) near the base flower 31 color. Petal color of this comparator is Red-Purple 62C.

BRIEF DESCRIPTION OF THE PHOTOGRAPHS

The accompanying photograph in FIG. 1 illustrates in full color a close-up view of a flower of the new cultivar. The plant producing this flower was approximately six months old, grown in a greenhouse during March in Camporosso, Italy.

Figure 2:
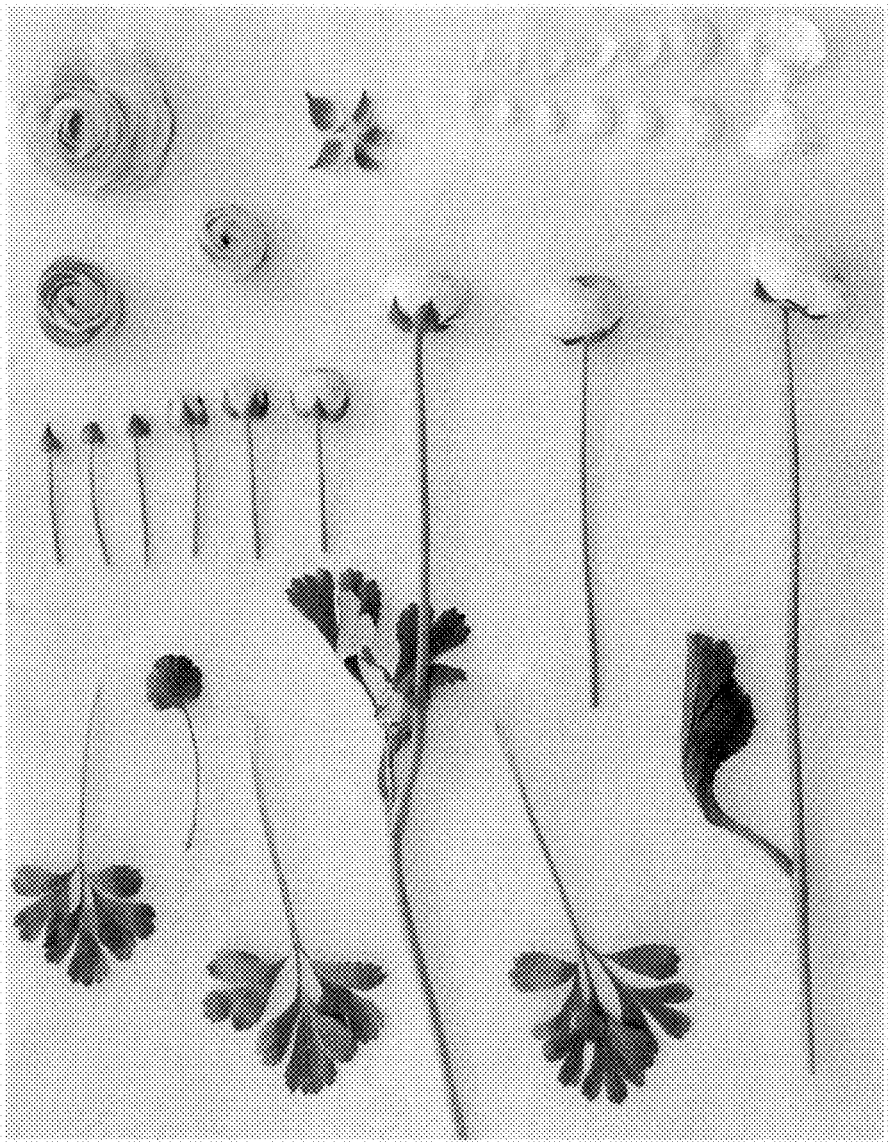

FIG. 2 illustrates various floral and foliar parts.

The photographs were taken using conventional techniques and although colors May appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe plants of 'AB TEPEYO' planted in the month of September in a greenhouse in Camporosso Mare, Italy. The plant has been described in the month of March. In order to protect the crop against pests, some chemical treatments are performed. Treatments with growth regulators can be performed to limit the plant sizes. In particular, no growth regulators have been applied on the plant described. The rhizome has been planted on raised benches in a peat and pumice substrate mixture. The growing temperature ranged from 12° C. to 25° C. during the day and from 2° C. to 8° C. during the night. General light conditions are bright, normal sunlight. Measurements and numerical values represent averages of typical plant types.

Botanical classification: *Ranunculus asiaticus* 'AB TEPEYO'

PROPAGATION

Time to Rooting: 15 days at approximately 10-12° C.

Time to produce a rooted plantlet: 20 days.

Root Description: Secondary roots grow by rhizome and are fasciculate type.

PLANT

Age of the Plant Described: About 5 months.

Growth Habit: Herbaceous perennial, robust plant, semi-prostrate vegetation

Height to top flower: 45 to 55 cm.

Plant Spread: 25 to 35 cm.

Branching Characteristics: Main floral stems grow from a basal rosette with 1 lateral branches, which has 1 flowers.

Length of Lateral Branches: 45 to 50 cm.

Diameter of Lateral Branches: 0.4 to 1.0 cm.

Texture of Lateral Branches: Glossy, slightly tomentose.

Internode length: No internodes, basal rosette.

Strength of lateral branches: Moderate.

Color of Lateral Branches: Strong Yellow Green (RHS 144A).

Angle of branches: 25° to 30°.

Number of Leaves per Lateral Branch: Usually 2 or 4.

FOLIAGE

Plants have marked heterophyllia in relation to the degree of their development and their position on the plant (base of the plant; floral stem). The same plant may have leaves of different size and arrangement (simple, ternate and biternate), in relation to the degree of development (young leaf and mature leaf) and their position on the plant.

Leaf at the base of the plant:

*Arrangement.*—Simple-Biternate young leaf; Biternate mature leaf.

*Average Length.*—18-25 cm.

*Average Width.*—10-15 cm.

*Overall Shape of blade.*—Obovate (young leaf); Palmatipartite (mature leaf).

*Dissected leaves, describe lobes, quantity of dissection.*—The young leaves are generally not lobed, while the mature leaves are typically divided into 3 sections, each of which is further subdivided into 3 lobes.

*Apex.*—Acute.

*Base.*—Attenuate.

*Attachment.*—Petiolate.

*Margin.*—Dentate.

*Texture of top surface.*—Slightly tomentose.

*Texture of bottom surface.*—Slightly tomentose.

*Appearance of top surface.*—Glossy.

*Appearance bottom surface.*—Glossy.

*Leaf internode length.*—The internodes are extremely close together, forming a basal rosette.

*Color.*—Young foliage upper side: Moderate Olive Green (RHS 146A). Young foliage under side: Moderate Yellow Green (RHS 147B). Mature foliage upper side: Moderate Olive Green (RHS 146A). Mature foliage under side: Moderate Yellow Green (RHS 147B).

*Venation.*—Type: Dichotomous; plunging into the limb at the upper surface; raised on the limb at the lower surface. Venation color upper side: Strong Yellow Green (RHS 144A). Venation color under side: Strong Yellow Green (RHS 144A).

*Petiole.*—Petiole: Slightly flattened Length: 10-15 cm. Diameter: 0.3-0.6 cm. Pubescence: Slightly tomentose. Color: Strong Yellow Green (RHS 144A).

Leaf inserted at the nodes of the floral stems:

*Arrangement.*—Biternate.

*Average Length.*—12-20 cm.

*Average Width.*—12-14 cm.

*Overall Shape of blade.*—Palmatipartite.

*Dissected leaves, describe lobes, quantity of dissection.*—Generally divided in 3 parts, each one of which further divided in in ⅔ deep incised lobes.

*Apex.*—Acute.

*Base.*—Attenuate.

*Attachment.*—Petiolate.

*Margin.*—Dentate.

*Texture of top surface.*—Slightly tomentose.

*Texture of bottom surface.*—Slightly tomentose.

*Appearance of top surface.*—Matte.

*Appearance bottom surface.*—Glossy.

*Leaf internode length.*—8-16 cm.

*Color.*—Foliage upper side: Moderate Olive Green (RHS 146A). Foliage under side: Moderate Yellow Green (RHS 147C).

*Venation.*—Type: Dichotomous, plunging into the limb at the upper surface and raised on the limb at the lower surface. Venation color upper side: Strong Yellow Green (RHS 144A). Venation color under side: Strong Yellow Green (RHS 144A).

*Petiole.*—Petiole: Slightly flat. Length: 4-6 cm. Diameter: 0.6-0.8 cm. Pubescence: Slightly tomentose. Color: Strong Yellow Green (RHS 144A).

FLOWER

Bloom Period: Winter-Spring.

Vase Life (cut flower): 10-15 days.

Persistent or Self-Cleaning: Self-Cleaning.

Bud:

*Closed bud.*—Shape: Flattened globular with an acute apex. Length: 1.8-2.0 cm. Diameter: 1-1.8 cm. Color: Moderate Yellow Green (RHS 137C) at the center; Strong Yellow Green (RHS 144A) where sepals start to overlap, along the venations and near the base.

*Slightly open bud.*—Shape: Flattened globular. Length: 1.8-2.2 cm. Diameter: 2.0-2.4 cm. Color: Light Yellowish Pink (RHS 37D).

Flower size:

*Diameter.*—6-10 cm.

*Height.*—3-4.5 cm.

Corolla: Round, symmetrical, flattened.

*Petals.*—

*Arrangement.*—Imbricated, disposed on the receptacle in very tight verticils. The size of the petals is quite variable. according to the position in the corolla. decreasing from the exterior toward the center. The average size of fully developed petal is as follows:

*Petal Length.*—3.5-5.5 cm.

*Petal Width.*—3.0-6 cm.

*Quantity.*—Double flower, petals are very numerous (>100).

*Texture.*—Silky, thin. Resistant to tearing.

*Petal Apex.*—Rounded.

*Petal shape.*—Obovate.

*Margin.*—Entire-Finely Crenate.

*Aspect.*—Concave with moderately reflexed apex when flower is fully opened.

*Color when opening.*—

*Upper surface.*—Light Yellowish Pink (RHS 37D).

*Lower surface.*—Light Yellowish Pink (RHS 37D).

*Color Fully opened.*—

*Upper surface.*—Light Yellowish Pink (RHS 37D) with a Deep Pink (RHS 48BD) border and Light Yellow Green (RHS 145D and 154D) near the base

*Lower surface.*—Light Yellowish Pink (RHS 38D) with a Deep Pink (RHS 48BD) border and Light Yellow Green (RHS 145D and 154D) near the base Calyx-Sepals(S):

*Quantity per flower.*—5.

*Shape.*—Concave incurved at the apex.

*Length.*—2.5-3.5 cm.

*Width.*—1.5-2.5 cm.

*Apex.*—Slightly acute to rounded.

*Base.*—Truncate.

*Margin.*—Entire.

*Texture.*—Lower surface is tomentose; Upper surface is glabrous.

*Color Upper Surface.*—Strong Yellow Green (RHS 144A); Light Yellow Green (RHS 145B) at the base.

*Color Lower Surface.*—Moderate Yellow Green (RHS 146D); Moderate Olive Green (RHS 146A) along the venations and Strong Yellow Green (RHS 144A) near the base.

Peduncle: None

Pedicel:

*Length.*—30-35 cm.

*Diameter.*—0.4-1.0 cm.

*Color.*—Strong Yellow Green (RHS 144A).

*Orientation.*—Upright. Straight, rigid.

*Pubescence.*—Slightly tomentose.

Fragrance: None

REPRODUCTIVE ORGANS

Androecium: Stamens are almost completely transformed to petals. Very infrequently small, malformed stamens can be found in some flowers at the end of the flowering.

Gynoecium: The pistils are numerous, short, locked together at the center of the corolla in a Dark Red (RHS 59A)/Dark Purplish Red (RHS N79B) dome-shaped apocarpous gynoecium.

Nectar glands: Absent.

OTHER CHARACTERISTICS

Disease and Pests: Neither resistance nor susceptibility observed.

Drought Tolerance and Cold Tolerance: No differences have been noted in comparison to the common tolerance characteristics to other *Ranunculus* cultivars.

Fruit-Seed Production: Not observed.

What is claimed is:

1. A new and distinct cultivar of *Ranunculus* plant named 'AB TEPEYO' as herein illustrated and described.

* * * * *